United States Patent
Tkaczyk et al.

(10) Patent No.: US 7,415,093 B2
(45) Date of Patent: Aug. 19, 2008

(54) METHOD AND APPARATUS OF CT CARDIAC DIAGNOSTIC IMAGING USING MOTION A PRIORI INFORMATION FROM 3D ULTRASOUND AND ECG GATING

(75) Inventors: John Eric Tkaczyk, Delanson, NY (US); Peter Michael Edic, Albany, NY (US); James W. LeBlanc, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/554,519

(22) Filed: Oct. 30, 2006

(65) Prior Publication Data
US 2008/0101532 A1  May 1, 2008

(51) Int. Cl.
*A61B 6/00* (2006.01)
(52) U.S. Cl. .............................. 378/8; 378/4
(58) Field of Classification Search ............... 378/8, 378/4, 901
See application file for complete search history.

(56) References Cited

U.S. PATENT DOCUMENTS

| | | | |
|---|---|---|---|
| 5,860,927 A * | 1/1999 | Sakaguchi et al. | 600/453 |
| 6,056,691 A * | 5/2000 | Urbano et al. | 600/443 |
| 6,223,073 B1 * | 4/2001 | Seegobin | 600/515 |
| 6,224,553 B1 * | 5/2001 | Nevo | 600/437 |
| 6,231,834 B1 * | 5/2001 | Unger et al. | 424/9.51 |
| 6,408,043 B1 * | 6/2002 | Hu et al. | 378/8 |
| 6,522,712 B1 * | 2/2003 | Yavuz et al. | 378/4 |
| 6,614,874 B2 | 9/2003 | Avinash | |
| 6,661,873 B2 | 12/2003 | Jabri et al. | |
| 6,792,072 B2 | 9/2004 | Avinash | |
| 6,934,352 B2 * | 8/2005 | Freytag et al. | 378/8 |
| 6,934,357 B2 | 8/2005 | Boyd et al. | |
| 7,068,826 B2 | 6/2006 | Jabri et al. | |
| 7,175,598 B2 * | 2/2007 | Yoneyama | 600/443 |
| 2004/0136490 A1 | 7/2004 | Edic et al. | |
| 2005/0080336 A1 * | 4/2005 | Byrd et al. | 600/428 |
| 2005/0149137 A1 * | 7/2005 | Chinchoy et al. | 607/25 |

\* cited by examiner

*Primary Examiner*—Courtney Thomas
*Assistant Examiner*—Alexander H Taningco
(74) *Attorney, Agent, or Firm*—Ziolkowski Patent Solutions Group, SC

(57) ABSTRACT

ECG and ultrasound data of the heart are acquired in real-time during a scan. A data acquisition module is controlled during the scan to prospectively gate acquisition of CT data as a function of the real-time ECG data and the real-time ultrasound data. An image is reconstructed from the acquired CT data.

22 Claims, 6 Drawing Sheets

METHOD AND APPARATUS OF CT CARDIAC DIAGNOSTIC IMAGING USING MOTION A PRIORI INFORMATION FROM 3D ULTRASOUND AND ECG GATING

BACKGROUND OF THE INVENTION

The present invention relates generally to diagnostic imaging and, more particularly, to correcting motion errors in imaging data acquired from an object prone to motion.

Various imaging modalities are useful to image objects in or prone to motion, such as the heart in cardiac studies. For example, in computed tomography (CT), magnetic resonance imaging (MRI) and other imaging modalities directed to the acquisition of data from an object prone to motion, one or more motion correction techniques are generally used to reduce motion-induced artifacts in the reconstructed images. In known studies, this motion correction or compensation can add significant complexity in post processing of the images.

In one specific example, CT imaging requires measurement of more than 180 degrees of projection data to formulate an image. Because of various limitations in conventional CT scanners, the time necessary to collect a complete set of projection data is significant relative to object motion. For example, cardiac CT imaging is typically performed with the aid of an electrocardiogram (ECG) signal, which is used to synchronize data acquisition and image reconstruction with the phase of minimal cardiac motion. The ECG signal collected from the patient represents the electrical properties of the heart and is helpful in identifying the quiescent period of cardiac activity, which is preferred for data acquisition. Moreover, the ECG signal assists in identifying this quiescent period over several cardiac cycles. By synchronizing data collection with the quiescent period of the cardiac cycle, image artifacts and spatial resolution due to heart motion are reduced. Additionally, by consistently identifying this quiescent period in successive cardiac cycles, inconsistencies between images acquired at different cardiac cycles are reduced. ECG signals can be used similarly in MR and other imaging modalities. The ECG signal can gate acquisition of projection (known as prospective gating) or may be used subsequent to data acquisition (known as retrospective gating) to identify the phase of the cardiac cycle with minimum motion. Prospective gating allows dramatic reduction in dose administered to the patient since projection data is not collected during phases of the heart having significant organ motion.

The conventional ECG gating described above does not provide mechanical motion detection. That is, while an ECG signal can indicate that motion is occurring, has occurred, or is about to occur, it is a boundary measurement (electrical signals within the heart are measured on the surface of a patient) and does not provide accurate real-time displacement data of the heart. Instead, mechanical motion of the heart must be inferred from the electrical activity measured in the ECG signal. Since actual mechanical motion, or displacement, of the heart contributes to sub-optimal image quality, cardiac images that depend solely on ECG signals often require significant post processing to correct for motion artifacts or often require a very high acquisition rate to minimize the extent of cardiac motion during acquisition.

CT reconstruction typically does not utilize a priori information on heart motion. In conventional ECG-gated cardiac CT studies, the heart is presumed to be a stationary object during the short acquisition period identified as the quiescent period in the acquired ECG signal (applicable to both prospective and retrospective gating techniques). Conventionally, half-scan imaging techniques (requiring a fraction of the time for one complete rotation of the gantry about the subject) are used to reduce the impact of motion; however, their effectiveness is less than optimal since half-scan weighting techniques used for image reconstruction combine CT projection data acquired at both extents the of angular range of data acquisition covering 180 degree plus the fan angle of the X-ray beam. The interpolation of projection data at both ends of the dataset is predetermined and, therefore, does not change based on each particular acquisition as needed since there is no a priori information available. For data collected roughly in the center of the angular range of projection data acquisition, the data is incorporated without any weighting. Further, even with a gantry speed of 0.3 s/rotation, the central region of the projection range constitutes a slightly larger than 150 ms temporal window, which is prohibitively slow to sufficiently "freeze" cardiac motion. The data acquisition window for CT systems having dual tube-detector assemblies is typically between 70 ms and 80 ms during which heart motion may occur. Ideally, a temporal window of 20 ms to 40 ms is needed to adequately freeze cardiac motion.

It would therefore be desirable to synchronize data acquisition and image reconstruction with cardiac phase and motion data to acquire and reconstruct substantially motion-free datasets and images.

BRIEF DESCRIPTION OF THE INVENTION

The present invention is directed to a method and apparatus for synchronizing data acquisition and image reconstruction with cardiac phase and motion data that overcome the aforementioned drawbacks. ECG data and ultrasound data are acquired in real-time and a data acquisition module is prospectively controlled to acquire CT data of the patient as a function of the real-time ECG data and the real-time ultrasound data.

Therefore, in accordance with one aspect of the present invention, a CT cardiac imaging system includes an ECG machine configured to output ECG data indicative of a cardiac cycle of a patient and an ultrasound machine configured to output ultrasound data indicative of at least one of a measured torsional, translational, rotational, and deformational motion of a heart of the patient. The system further includes a CT imaging apparatus having a data acquisition module with a rotatable gantry having a bore therethrough, the rotatable gantry having an x-ray source and an x-ray detector disposed therein to emit one of a fan beam of x-rays and a cone beam of x-rays toward the patient and receive x-rays attenuated by the patient, respectively. The CT imaging apparatus further includes a computer programmed to receive ECG data in real-time, receive ultrasound data in real-time, control the data acquisition module to acquire CT data of the patient as a function of the real-time ECG data and the real-time ultrasound data, and reconstruct an image from the acquired CT data.

In accordance with another aspect of the present invention, a method of cardiac imaging includes the step of acquiring ECG data and ultrasound data from a subject. The method further includes the steps of determining a CT data acquisition window from the acquired ECG data and ultrasound data, illuminating the patient with x-rays and acquiring CT data during the CT data acquisition window, and reconstructing an image using the acquired ECG data, ultrasound data, and CT data.

In accordance with yet another aspect of the present invention, a computer readable storage medium includes a computer program to adaptively control a CT cardiac imaging gating process and analyze gathered CT data. The computer program represents a set of instructions, that when executed by a computer, causes the computer to prospectively gate an x-ray source in a CT scanner during a CT scanning process into an expose state to illuminate a patient with x-rays based on real-time ECG data and real-time ultrasound data. The computer program further causes the computer to acquire CT data from the gated x-ray source and reconstruct the acquired CT data into an image.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE INVENTION

The present invention is directed to a method and apparatus for acquiring heart motion and heart phase data, and using this data to prospectively acquire CT imaging data of the heart. The heart motion data and heart phase data are also used for motion correction or compensation of the imaging data and for facilitating reconstruction of a CT image.

The present invention will be described with respect to a "third generation" CT scanner, but is equally applicable to other generations of CT system, as well as with other imaging modalities. Moreover, the present invention will be described with respect to an imaging system that includes a CT scanner that acquires image data, an ECG machine that acquires cardiac electrical data, and an ultrasound machine that acquires cardiac motion data from a patient. The CT scanner, ECG machine, and ultrasound machine are stand-alone devices that can be used independently from one another, but, as will be described, are configured to operate in tandem to acquire CT data, ECG data, and ultrasound data substantially simultaneously. It is also contemplated that the present invention is applicable with an integrated ECG/ultrasound/CT system. Moreover, although the invention talks about concurrent acquisition of ECG data, ultrasound data, and CT data, it is contemplated that one of either ECG data or ultrasound data can be utilized for the purposes described herein.

Figure 1:
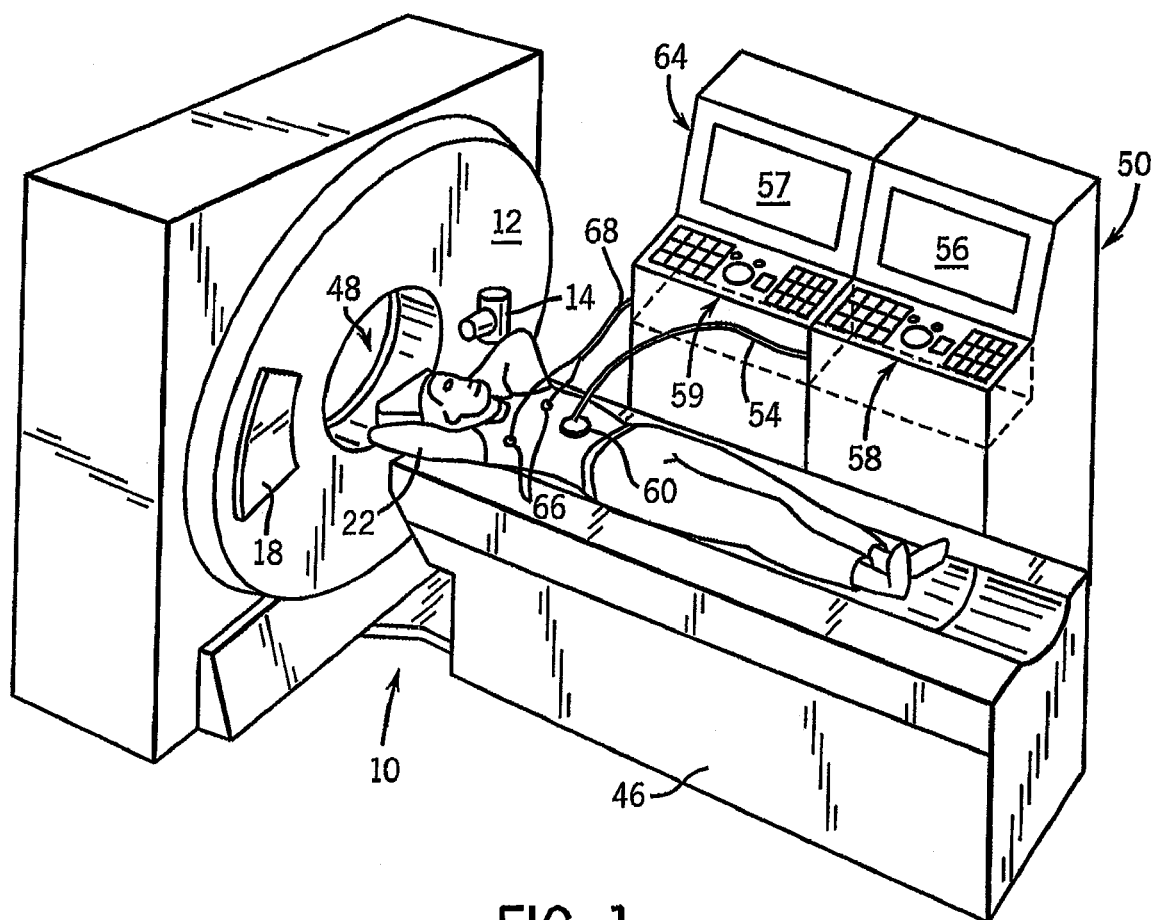
FIG. 1 is a pictorial perspective view of a CT cardiac imaging system according to the present invention.
Figure 2:
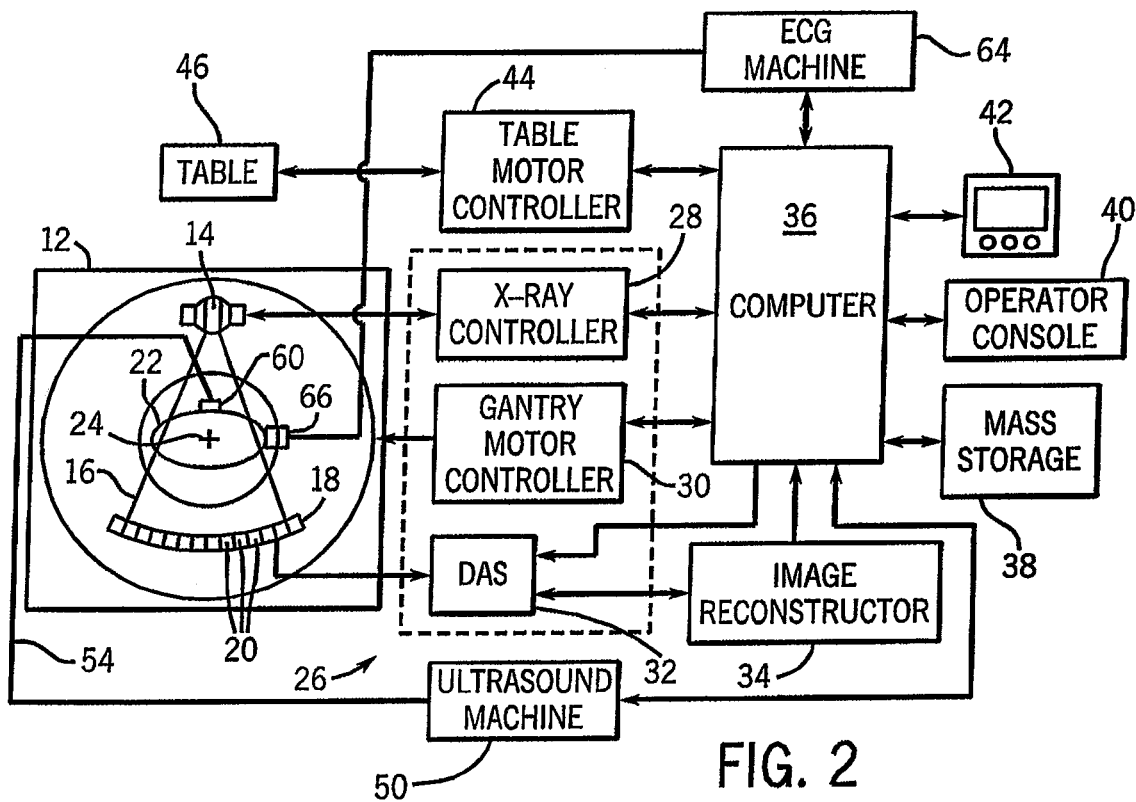
FIG. 2 is a block schematic diagram of the system illustrated in FIG. 1.

Referring to FIGS. 1 and 2, a computed tomography (CT) cardiac imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20, which together sense the projected x-rays that pass through or around a medical patient 22. Each detector 20 produces an electrical signal that represents the intensity of an impinging x-ray beam and hence the attenuated beam as it passes through the patient 22. The intensity data are processed to produce projection data, which represent the integral of linear attenuation coefficient along x-ray paths that traverse the patient. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high-speed reconstruction. The reconstructed image is applied as an input to a computer 36, which stores the image in an electronic mass storage device 38. The image reconstructor 34 may be a separate entity as shown in FIG. 2, or it may be hardware, firmware or software that resides inside computer 36. Moreover, the image reconstructor 34 may access mass storage 38 directly.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44, which controls a motorized table 46 to position patient 22 within gantry 12. Particularly, table 46 moves portions of patient 22 through a gantry opening 48.

Still referring to FIGS. 1 and 2, in an exemplary embodiment, an ultrasound machine 50 having one or more ultrasound array probes 60 linked thereto by control and readout cable 54 is used to acquire mechanical motion data. The ultrasound machine includes a printer (not shown) for printing images displayed on monitor 56 as well as a keyboard and other input devices 58 to carry out an ultrasound study. In a preferred embodiment, the ultrasound machine 50 is remotely positioned from the patient 22 and located at or near the operator console 40 of the CT scanner. Ultrasound array probes 60 are attached to patient 22 and obtain 3D ultrasound readings and images of the cardiac anatomy via a plurality of transducers in the ultrasound array probes 60.

Also shown in FIGS. 1-2, in an exemplary embodiment, is an ECG machine 64 having a plurality of leads 66 linked thereto by control and readout cable 68. The ECG machine also includes a monitor 57 for displaying images as well as a keyboard and other input devices 59 to carry out an ECG study. The ECG signal collected from the patient 22 is used to synchronize the acquisition of imaging data with the quiescent period of cardiac motion. The ECG signals can be diagnostic with respect to the presence of atypical, aperiodic, or erratic heart beats which otherwise can result in acquisitions without useful data. Often a drug can be administered to slow and calm the heart beats if the erratic condition exists and this application of a drug can be contingent on the ECG signals. In a preferred embodiment, the ECG machine 64 is remotely positioned from the patient 22 and located at or near the operator console 40 of the CT scanner 10. The ECG leads 66 are attached to the patient 22 in a manner well known in the art. The ECG leads 66 are also operatively connected to the computer 36 or ECG machine 64, to transmit readings thereto.

Figure 3:
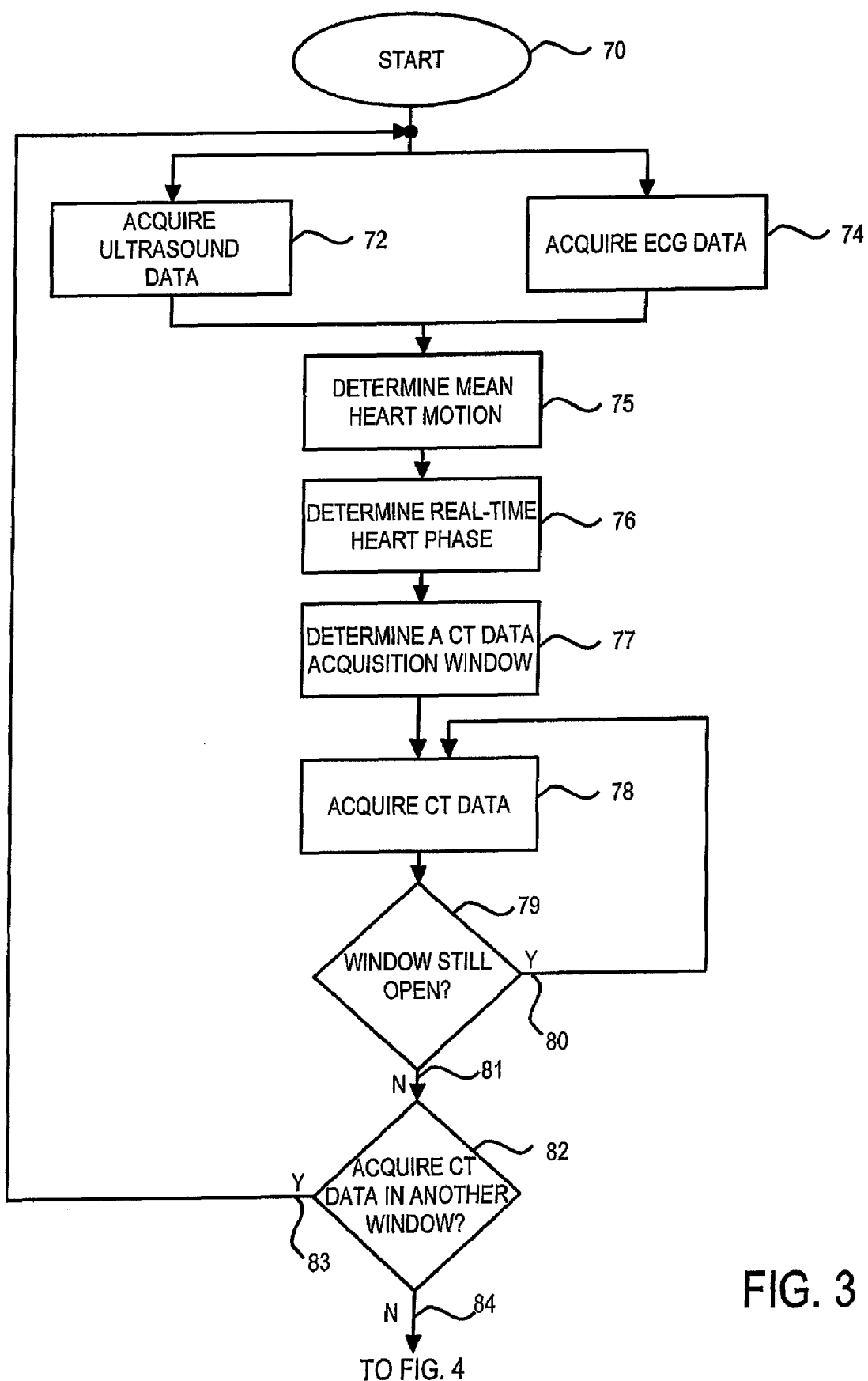
FIGS. 3-5 are a flowchart setting forth the process of CT cardiac imaging of the present invention.

Computer 36 is programmed to analyze acquired ECG data, ultrasound data, and CT image data, as well as reconstruct the data to achieve an optimal cardiac image. In FIG. 3, a flowchart setting forth steps of one exemplary technique for obtaining an optimal CT cardiac diagnostic image using ultrasound and ECG gating is shown. The technique begins at 70 and acquires 72 ultrasound data from a subject and acquires 74 ECG data from the subject. The ultrasound data acquired at 72 provides real-time information on the mechanical motion of the heart such as a translation of the heart from its resting position to a different position. The ECG data acquired at 74 provides real-time information on the electrical stimulation of the heart. Both types of information can indicate quiescent periods in the heart phase.

When analyzed, the acquired ultrasound data and ECG data provide several types of information. First, the ultrasound data is analyzed to determine a mean heart motion 75. That is, the ultrasound data acquired is analyzed over a period of time to examine heart position at each time during the cardiac cycle and over a period of many beats. As the position of the heart varies according to both a positional shift, rotation, scaling, and/or torsional motion, a mean heart motion is helpful in determining a characteristic behavior that later can be useful to aid in acquisition timing and data processing. Additionally, the ultrasound data and the ECG data are analyzed to determine 76 a real-time phase of the cardiac cycle.

The motion of the heart can be represented as the three-dimensional trajectory in time of strategic points of the heart anatomy. Of particular significance is the trajectory of each point along the coronary vessels, the outer walls of the myocardium and the inner walls lining the ventricles and atria. Alternately, the heart motion can be represented by the parameterization of a numerical model of the heart. The simplest heart model would capture features like the angular positions of the major axes of the heart (treating it like an ellipsoidal solid). In this way the positional, rotational, scaling, and torsional motions are captured by the parameterized motions of these axes. The mean motion of axes 75 is captured in the periodic variations and the real-time phase 76 of the cardiac cycle is represented by the real-time location along these mean variations. More realistic numerical models of the heart employ parameterized surfaces and volumetric solids that change shape and position over time with constraints representing the elastic and connective properties of the heart chambers, muscles and vessels. In either case the free parameters of the model are determined by comparison with the measured ultrasound data.

The ultrasound measurement generates multi-dimensional data of the imaged object over time, which can be used to fit the heart model. There is a correspondence between the heart model at each phase location and the expected ultrasound data. This correspondence will be maximized when the model parameters are optimum. Maximum likelihood estimation is a method used in the art to perform an optimization (or fit) between the model and the data. Similarly, the ECG data represents an electrical voltage signal trace over time that is periodic. The mean periodic variation averaged over many heartbeats is taken to indicate the mean motion 75 and the real-time voltage to indicate the real-time phase 76.

From the determination of the mean heart motion 75 and the real-time phase of the cardiac cycle 76, a CT data acquisition window is determined 77. The CT data acquisition window is representative of the quiescent periods in the determined real-time phase of the cardiac cycle that exhibit heart motion where the heart is relatively stationary. The magnitude of motion correction required for CT image reconstruction is reduced if the CT acquisition window occurs during this "minimal-motion" phase of the cardiac cycle. During the CT data acquisition window, x-ray source 14 is enabled to administer x-ray beams 16 to the patient 22 in the form of a fan or cone while CT data is acquired 78. The acquired CT data, the ultrasound data, and the ECG data are stored to an electronic mass storage device 38 for later retrieval. After CT data has been stored, a determination is then made of whether the CT data acquisition window is still open 79. If it is 80, the process returns to acquire additional requisite CT data 78 required for CT image reconstruction. If the acquisition window is closed 81, a determination is then made whether additional CT data is required for image reconstruction 82.

The need for a complete CT data set before reconstruction is determined by whether a full set of projection data at required gantry angle positions has been acquired. For a half-scan reconstruction, the angular range of projection data acquisition may be 240 degrees. Each acquisition window generates some or all of the data, which can fill this angular range. When the full angular range of projection is acquired upon one or more heartbeats, then reconstruction can commence. It is also contemplated that image reconstruction can begin as soon as the first projection data set has been acquired. This procedure can be implemented in software as an internal table of zero-valued entries, each entry for one degree of the angular range. Upon completion of a portion of the angular range of required projection data acquisition, the corresponding portion of the table is filled with a unity value. The full population of the table or a sufficient sum over the table triggers the passage to a reconstruction mode. This approach is typical of acquisition protocols used with multi-sector reconstruction techniques. However, the acquisition window can be prescribed such that projection data suitable for image reconstruction is acquired during one acquisition, which is typical of acquisition protocols utilized with segment reconstruction techniques.

If more CT data (either to complete the projection data required for the current acquisition, or to acquired data for another section of cardiac anatomy) is required 83, the process returns to the start state 70 and repeats as described above. If it has been determined that sufficient data has been acquired 84, CT scanning is terminated, and image reconstruction, described below with respect to FIGS. 4 & 5, begins.

Figure 4:
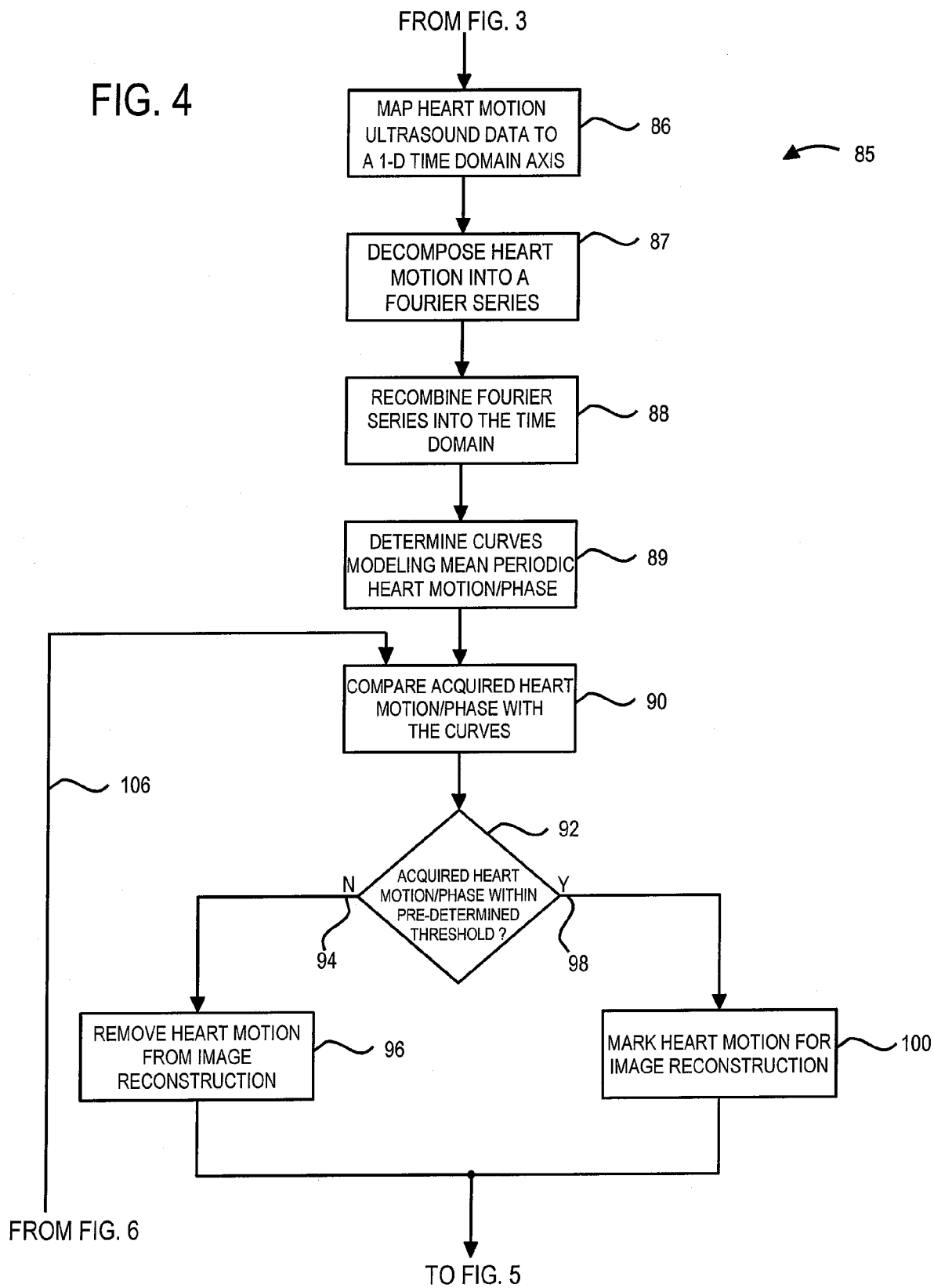
Figure 5:
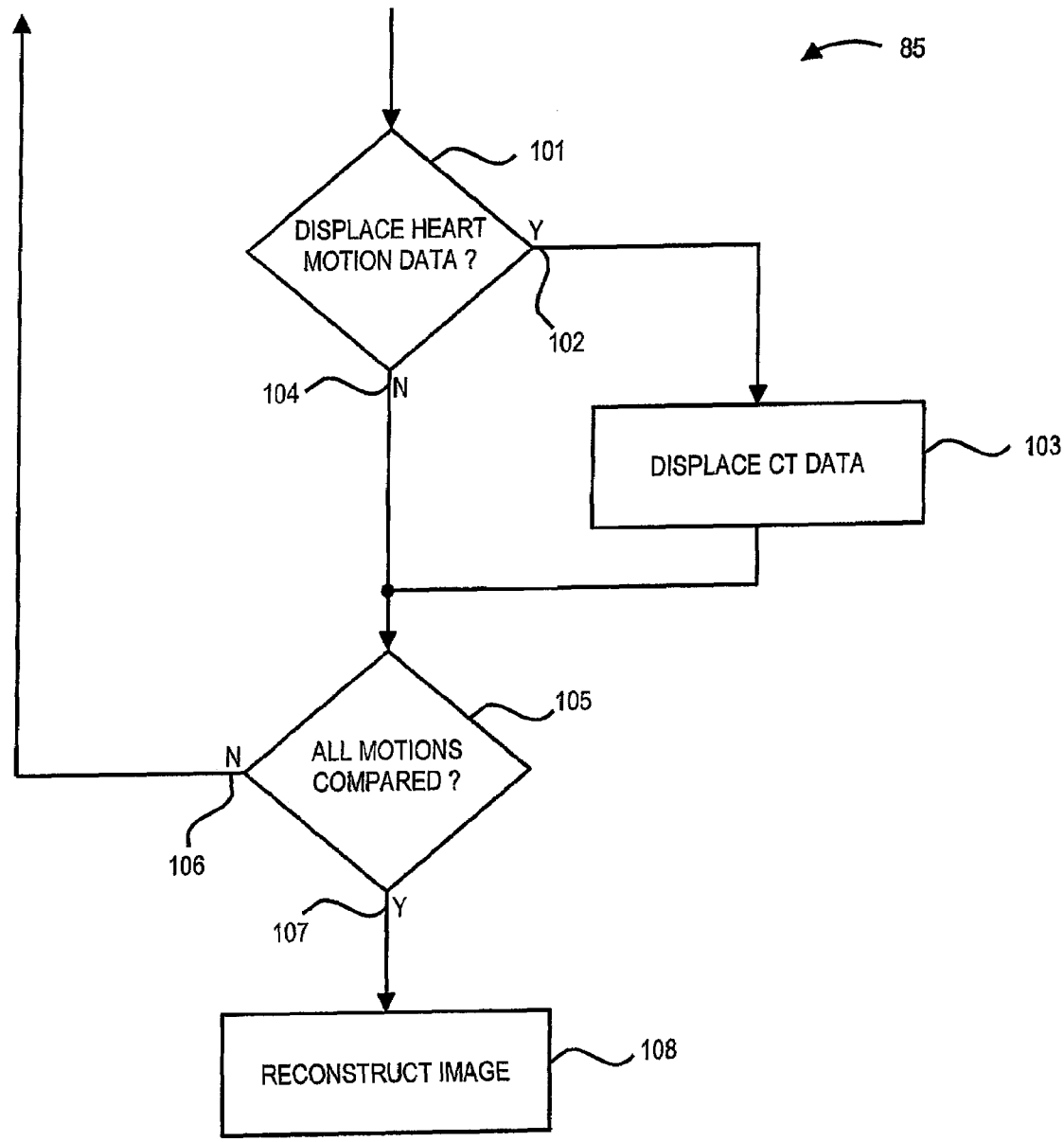

FIGS. 4 & 5 show a reconstruction process 85 for reconstructing an optimal cardiac image from the acquired ECG data, ultrasound data, and acquired CT data. In reconstructing the acquired CT data, any atypical cardiac data acquired is preferably identified and removed before reconstructing an image in order to obtain an image of optimal quality. The identification of atypical cardiac data is achieved by analyzing the ultrasound data to detect non-periodic heart motions and by analyzing the ECG signal to determine atypical electrical activity within the heart. It is contemplated that real-time analysis of the ECG and ultrasound signals would identify these regions and trigger the CT system to repeat the acquisition of projection data for the corresponding angular range. As shown in FIG. 4, detection of non-periodic heart motions is accomplished by first mapping heart motion measured in the ultrasound data on a one-dimensional time domain axis 86 and decomposing it into a Fourier series 87. For example, this mapping of ultrasound data to the one-dimensional time domain can be accomplished by utilizing one of the significant parameters (or combinations thereof) in the 4D heart model. As explained above, the heart model is fit to the ultrasound data and the model parameters are representative of the heart motion. The periodic repetition of this parameter is captured by the lower frequency peaks in the Fourier series. The Fourier series is then truncated (i.e. set to zero) at higher frequencies and recombined into the time domain 88, which results in a recovery of the mean periodic cardiac motion for a specific time frame. A curve for representing the mean periodic cardiac motion is then determined 89 from the recombination. The process of determining a mean periodic heart motion 89 utilizing Fourier curve modeling 86-88 can be done off-line from the acquisition and reconstruction process, and as such, many heart beats can be included in this averaging procedure. Furthermore, although steps in FIG. 4 are depicted utilizing Fourier techniques, comparable techniques can be accomplished using the temporal signals themselves, as is well known in the art. For example, Fourier-based signal processing can be implemented in the temporal domain using linear system theory, as is also well known in the art. A metric can determine whether the heartbeat is sufficiently stable to proceed with the CT acquisition (i.e., it can be used as a prognostic indicator of heart rate/motion variability). The physician can decide to administer a heart-calming drug if the aperiodic characteristics in the signal are significant. Referring back to FIG. 4, the mean periodic heart motion is compared to the motion recorded during the CT scan 90. The ECG signal itself is a one-dimensional time curve that can similarly be analyzed using Fourier-based or time-based signal processing techniques to determine a mean periodic ECG trace/curve 89 that is used to detect atypical behavior or establish the phase of the heart at any time instant.

As stated above, the reconstruction process 85 compares 90 a local section of an acquired heart motion with the mean periodic cardiac motion in the modeled motion curve and determines 92 whether the local section of an acquired heart motion falls within a pre-determined threshold of the modeled motion curve. Similarly, a local section of an acquired heart phase is compared 90 to the curve modeling mean periodic heart phase. In this manner, atypical heartbeats characterized by atypical heart motion and/or an atypical cardiac phase may be identified and removed from image reconstruction.

Figure 6:
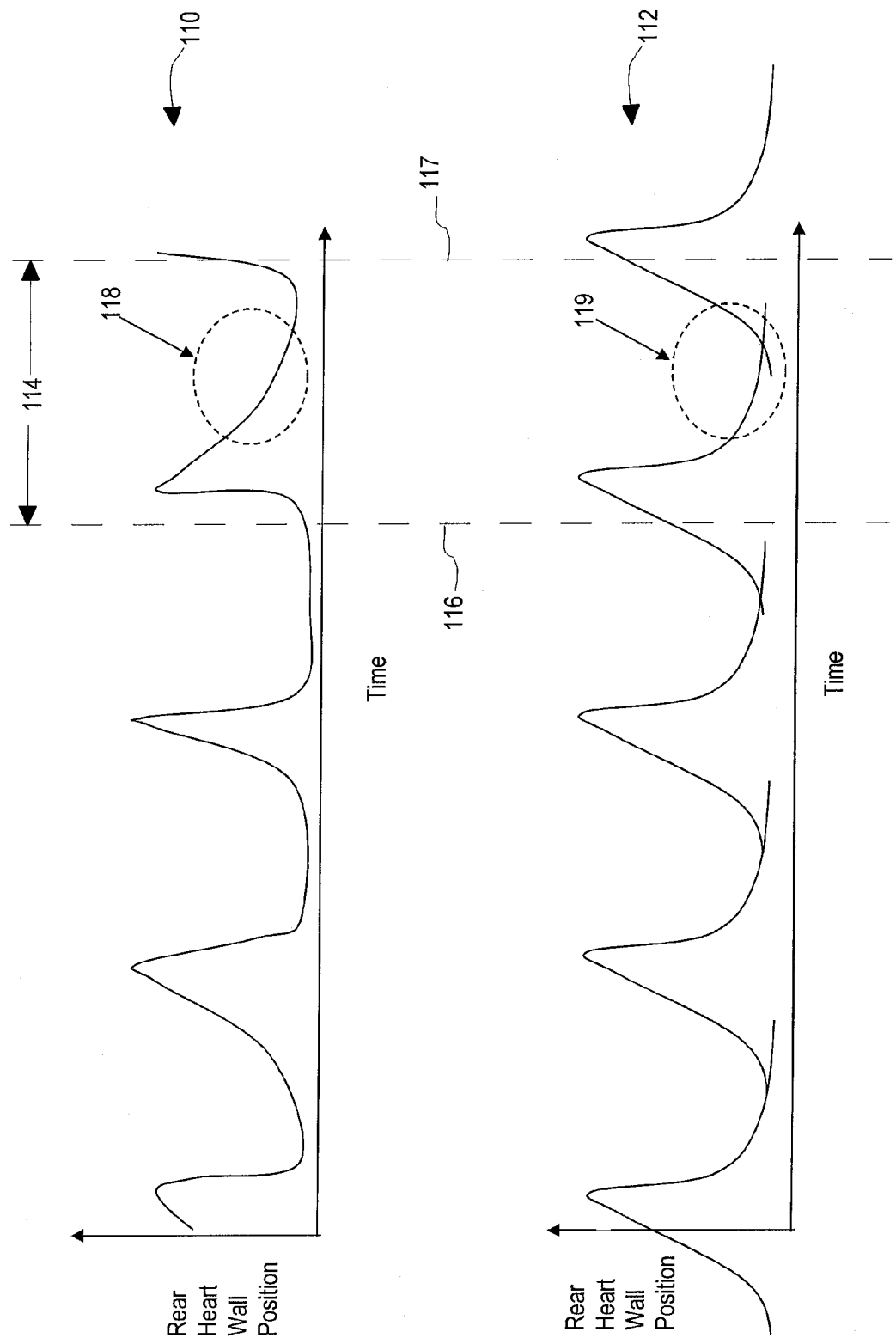
FIG. 6 is a graphical view comparing an acquired heart motion to a mean heart motion as set forth in the present invention.

An atypical heart motion is shown in FIG. 6. Portions of a plot 110 of acquired rear heart wall position and a plot 112 of the mean periodic heart wall position, each acquired and determined as described above, are shown graphed as a function of time. The one-dimensional plot 110 of the acquired mean rear heart wall position versus time can be represented as an infinite sum of sine and cosine functions that are harmonically related, i.e. a Fourier series. On a temporally local basis, it is possible to correlate the acquired rear heart wall position 110 with the recomposed, mean periodic cardiac motion 112 to determine similarity. That is, heart wall position for an acquired heartbeat can be measured for a local section 114 between a first time 116 and a second time 117, the local section 114 defining a measured heartbeat. The heart wall position during the quiescent period of the local section 114 can then be compared to the mean heart wall position during the quiescent period for the local section 114, and any variance 118, 119 between the acquired and mean wall positions can be measured to determine if the variance 118, 119 exceeds or falls within a pre-determined threshold.

Referring again to FIG. 4, if the beat or local section 114 of FIG. 6 of an acquired heart motion does not fall within the pre-determined threshold 94, then the acquired heat beat is removed from image reconstruction 96. If, however, the beat of the acquired heart motion falls within the pre-determined threshold 98, then the beat is marked for image reconstruction 100.

As a further constraint on image reconstruction, it is also envisioned that the phase of the cardiac cycle for an acquired heart beat using the ECG data is also compared 90 to a modeled curve. The phase of the cardiac cycle for a local section of an acquired heart behavior is compared to the corresponding mean heart behavior. Thus, in this comparison, it is determined if the phase of a local section of the acquired heart behavior matches with the corresponding mean phase of the cardiac cycle within a certain set window. If the phase of the cardiac cycle for a local section of an acquired heart behavior is not consistent with the cardiac cycle for the mean heart behavior, then the heartbeat is removed from image reconstruction 96. If, however, the phase of the cardiac cycle of the acquired heartbeat matches that of the mean cardiac phase for a local section, then the heartbeat is marked for image reconstruction 100.

For those beats that are marked to be included in image reconstruction 100, the acquired ultrasound data and associated fit model corresponding to those heart beats is also used as a consistency condition for the CT image reconstruction. The ultrasound data acquired over these beats measuring heart motion and position are compared to a mean heart motion and position as determined by the ultrasound data acquired over many beats. Referring now to FIG. 5, a determination 101 is made whether any displacement of the CT data is needed to shift it into alignment with the mean. If displacement is needed 102, the CT data is displaced 103 by an amount of displacement or deformation to shift the heart position for the measured beat to substantially match the mean heart position. The reconstruction process utilizes the mean and differential motion and positional information to modify the back-projection step of the reconstruction process. (This technique is generally denoted as "Displace CT data" 103 in FIG. 5.) The raw ultrasound data and raw CT sinogram data are themselves in different domains and not easily compared. Therefore, the use of a numerical heart model which is fit to the mean ultrasound data and which can also be reprojected using the CT system model is a bridge to insure consistency between the ultrasound data and the CT data. Alternately, the properly scaled, ultrasound images are compared directly to the reconstructed CT images in order to calculate a metric representing the degree of registration at edges and volumes in the heart anatomy. The registration metric compared to some threshold determines the need for displacement or deformation of the image grid used to reconstruct the CT data. Specific anatomical features of diagnostic interest, such as the outer myocardium surface upon which the coronary vessels ride, would be the specific features compared to calculate such registration metrics. The displacements or deformations would then best be utilized to create CT reconstruction images where these specific anatomic features of interest are most accurately reproduced. For example, such regions of the image would be available to higher resolution inspection. Other areas of the heart with less diagnostic interest would be less accurately reproduced in the images, but with sufficient accuracy to satisfy the non-local requirements of the reconstruction algorithm.

Following displacement 103 of the CT data or if displacement is not needed 104, process 85 then determines 105 whether all acquired heart motions have been compared to the motion curve representing mean periodic heart motion. If not all heart motions have been compared 106, process 85 returns to step 90 to compare additional acquired heart beats. If all heart motions have been compared to the motion curve 107, a CT image is reconstructed 108 from the marked heart motion data according to known image reconstruction techniques, where the reconstruction grid is deformed as needed on a view-by-view basis to properly capture the measured motion information.

The CT imaging process described above utilizes real-time acquisition of ECG and ultrasound data to prospectively gate CT data acquisition and identify typical and atypical heart beats for reconstruction purposes. Furthermore, the CT imaging process is able to deform and displace acquired CT data, i.e. deform the reconstruction grid used during the back-projection process of CT image reconstruction, by comparing acquired ultrasound data representative of heart motion for an acquired local section to the mean periodic heart motion, thus providing a high resolution reconstructed CT image that minimizes image artifacts.

Additionally, the ultrasound data acquired in the imaging process described above may be used to produce a 3D image of the heart (i.e., the myocardial surface). In this manner, motion displacement and deformation of the CT data is obtainable for the entire heart surface. That is, for each heart wall/section, ultrasound data regarding heart position can be compared to the mean heart position for that wall/section. Upon combination thereof, a determination of a position variation of the entire heart surface from one beat to a mean heart surface position can be made. Likewise, the corresponding displacement of CT data for each of these heart walls/sections results in a CT image of the entire myocardial surface using both the mean motion signal and the temporally localized motion signal, which captures differential motion information. Accurate displacement of the acquired CT data allows for reconstruction of an optimal CT cardiac image having fewer image artifacts and higher resolution of the heart surface.

Ultrasound is a real-time imaging modality and provides accurate and near-instant information on the mechanical state of an object in motion, such as the heart. In the context of cardiac imaging, ultrasound can provide real-time information as to the size, shape, and location of the heart when it is in diastole, systole, or other phases of the cardiac cycle. Moreover, using Doppler imaging techniques that are well known in the art, displacement information over the volume of the heart can be measured. When combined with simultaneous acquisition of ultrasound data and CT data, the ultrasound data provides information on the shape, location, and deformation of the heart allowing compensation for the motion-and reducing motion-induced artifacts in the CT imaging reconstruction. Ultrasound can further provide data regarding a mean heart position for each phase of the heart and, when used in combination with ECG, provide synchronized mechanical motion data with the heart phase data to allow determination of the quiescent period of cardiac activity. In this manner, the combination of ultrasound data and ECG data makes it possible to reduce x-ray dosage to a patient by prospectively gating CT data acquisition to those heartbeats that are within certain pre-determined thresholds of heart motion and heart phase. X-ray dosage to a patient may further be reduced by configuring the CT imaging system to extrapolate and displace acquired CT data, thus allowing for the CT imaging system to integrate a wider range of acquired CT data into image reconstruction.

Therefore, in accordance with one embodiment of the present invention, a CT cardiac imaging system includes an ECG machine configured to output ECG data indicative of a cardiac cycle of a patient and an ultrasound machine configured to output ultrasound data indicative of at least one of a measured torsional, translational, and rotational, and deformational motion of a heart of the patient. The system further includes a CT imaging apparatus having a data acquisition module with a rotatable gantry having a bore therethrough, the rotatable gantry having an x-ray source and an x-ray detector disposed therein to emit one of a fan beam and a cone beam of x-rays toward the patient and receive x-rays attenuated by the patient. The CT imaging apparatus further contains a computer programmed to receive ECG data in real-time, receive ultrasound data in real-time, control the data acquisition module to acquire CT data of the patient as a function of the real-time ECG data and the real-time ultrasound data, and reconstruct an image from the acquired CT data.

In accordance with another embodiment of the present invention, a method of cardiac imaging includes the steps of acquiring ECG data and ultrasound data from a subject. The method further includes the steps of determining a CT data acquisition window from the acquired ECG data and ultrasound data, illuminating the patient with x-rays and acquiring CT data during the CT data acquisition window, and reconstructing an image from the acquired ECG data, ultrasound data, and CT data.

In accordance with yet another embodiment of the present invention, a computer readable storage medium includes a computer program to adaptively control a CT cardiac imaging gating process and analyze gathered CT data. The computer program represents a set of instructions, that when executed by a computer, causes the computer to prospectively gate an x-ray source in a CT scanner during a CT scanning process into an expose state to illuminate a patient with x-rays based on real-time ECG data and real-time ultrasound data. The computer program further causes the computer to acquire CT data from the gated x-ray source and reconstruct the acquired CT data into an image.

The present invention has been described in terms of the preferred embodiment, and it is recognized that equivalents, alternatives, and modifications, aside from those expressly stated, are possible and within the scope of the appending claims. Moreover, the present invention has been described in terms of medical imaging; however, the techniques described herein apply equally to imaging of inanimate objects.

What is claimed is:

1. A CT cardiac imaging system comprising:
    an ECG machine configured to output ECG data indicative of a cardiac cycle of a patient;
    an ultrasound machine configured to output ultrasound data indicative of at least one of a measured torsional, translational, rotational, and deformational motion of a heart of the patient; and
    a CT imaging apparatus comprising a data acquisition module including a rotatable gantry having a bore therethrough designed to receive the patient being translated through the bore by a movable table, the rotatable gantry having an x-ray source and an x-ray detector disposed therein to emit one of a fan beam of x-rays and a cone beam of x-rays toward the patient and receive x-rays attenuated by the patient, respectively, and the CT imaging apparatus further comprising a computer programmed to:
        receive the ECG data from the ECG machine in real-time;
        receive the ultrasound data from the ultrasound machine in real-time;
        control the data acquisition module to acquire CT data of the patient as a function of the real-time ECG data and the real-time ultrasound data; and
        reconstruct an image from the acquired CT data.

2. The CT cardiac imaging system of claim 1 wherein the computer is further programmed to:
    analyze the real-time ECG data to determine a heart phase therefrom; and
    analyze the real-time ultrasound data to determine a mean periodic heart motion therefrom.

3. The CT cardiac imaging system of claim 2 wherein the computer is further programmed to acquire CT data during an acquisition window based on the determined heart phase and the determined mean periodic heart motion.

4. The CT cardiac imaging system of claim 1 wherein the computer is further programmed to begin image reconstruction when a sufficient amount of CT data has been acquired.

5. The CT cardiac imaging system of claim 1 further comprising a memory storage device and wherein the computer is further programmed to store the acquired CT data, the ultrasound data, and the ECG data on the memory storage device.

6. The CT cardiac imaging system of claim 1 wherein the computer is further programmed to:
analyze the ultrasound data; and
detect non-periodic heart motion in the analyzed ultrasound data.

7. The CT cardiac imaging system of claim 1 wherein the computer is further programmed to:
map heart motion of the ultrasound data to a one-dimensional time domain axis
decompose the heart motion using Fourier analysis to obtain Fourier data;
transform the Fourier data into the time domain; and
determine a curve representing mean periodic cardiac motion.

8. The CT cardiac imaging system of claim 7 wherein the computer is further programmed to:
compare an acquired heart motion with the curve representing mean periodic cardiac motion; and
remove projection data associated with the compared acquired heart motion from the image reconstruction process if the compared acquired heart motion is outside of a predetermined threshold.

9. The CT cardiac imaging system of claim 1 wherein the computer is further programmed to:
compare an acquired heart phase with a curve representing mean periodic cardiac phase; and
remove projection data associated with the compared acquired heart phase from image reconstruction if the compared acquired heart phase is outside of a predetermined window.

10. The CT cardiac imaging system of claim 7 wherein the computer is further programmed to:
compare an acquired heart motion with the curve representing mean periodic cardiac motion;
determine a positional variation of a portion of acquired CT data based on the corresponding position variation between the acquired heart motion and the curve representing mean periodic cardiac motion; and
displace the acquired CT data to reduce image artifacts resulting from the positional variation.

11. A cardiac imaging method comprising the steps of:
acquiring ECG data from a subject during an image scanning sequence;
acquiring ultrasound data from the subject during the image scanning sequence;
determining a CT data acquisition window based on the acquired ECG data and the acquired ultrasound data;
illuminating the subject with x-rays within the CT data acquisition window;
acquiring CT data generated from the x-rays; and
reconstructing an image from the acquired ECG data, the acquired ultrasound data, and the acquired CT data.

12. The method of claim 11 wherein the step of acquiring ultrasound data further comprises attaching an ultrasound array probe to the subject in a manner that allows for measuring quality ultrasound images.

13. The method of claim 11 wherein determining a CT data acquisition window further comprises the steps of:
analyzing the ECG data and the ultrasound data;
determining a heart phase from the analyzed ECG data; and
determining a mean periodic heart motion from the analyzed ultrasound data.

14. The method of claim 11 further comprising the steps of:
analyzing the ultrasound data; and
detecting non-periodic heart motion in the analyzed ultrasound data.

15. The method of claim 14 wherein detecting non-periodic heart motion further comprises the steps of:
mapping heart motion of the ultrasound data to a one dimensional time axis;
decomposing the motion using Fourier analysis to obtain Fourier data;
transforming the Fourier data into the time domain; and
determining a curve representing the mean periodic heart motion.

16. The method of claim 15 further comprising the steps of:
comparing an acquired heart motion with the curve representing mean periodic cardiac motion; and
removing projection data associated with the compared acquired heart motion from image reconstruction if the compared acquired heart motion is outside a pre-determined threshold.

17. The method of claim 11 further comprising the steps of: comparing an acquired heart phase with a curve representing mean periodic cardiac phase; and
removing projection data associated with the compared acquired phase information from image reconstruction if the compared acquired heart phase is outside a pre-determined threshold.

18. A computer readable storage medium having a computer program to adaptively control a CT cardiac imaging gating process and analyze gathered CT data, the computer program representing a set of instructions that when executed by a computer causes the computer to:
prospectively gate an x-ray source in a CT scanner during a CT scanning process into an expose state to illuminate a patient with x-rays based on real-time ECG data and real-time ultrasound data;
acquire CT data from the gated x-ray source; and
reconstruct the acquired CT data into a cardiac image.

19. The computer readable storage medium of claim 18 wherein the set of instructions further causes the computer to:
map the ultrasound data representative of cardiac motion to a one-dimensional time domain axis;
decompose the cardiac motion using Fourier analysis to obtain Fourier data;
transform the Fourier data into the time domain; and
determine a curve representing mean periodic cardiac motion.

20. The computer readable storage medium of claim 19 wherein the set of instructions further causes the computer to:
compare an acquired cardiac motion with the curve representing mean periodic cardiac motion; and
remove projection data associated with the compared acquired cardiac motion from image reconstruction if the compared acquired cardiac motion is outside of a pre-determined threshold.

21. The computer readable storage medium of claim 18 wherein the set of instructions further causes the computer to:
determine a heart phase based on the real-time ECG data; and compare the heart phase relative to a curve representing mean cardiac phase to identify CT data to include in an image reconstruction of the cardiac image.

22. The computer readable storage medium of claim 20 wherein the set of instructions further causes the computer to:

obtain a 3D model of a heart surface position as a function of time based on the real-time ultrasound data;

determine a variation of the heart surface position from one beat to a mean heart surface position as measured over a plurality of beats; and displace the acquired CT data using both the mean heart surface position and the differential heart surface position relative to the mean heart surface position.

* * * * *